United States Patent [19]
Matolcsy et al.

[11] 3,953,427
[45] Apr. 27, 1976

[54] PROCESS FOR THE PREPARATION OF SUBSTITUTED S-ALKYL THIO-CARBAMATES

[75] Inventors: György Matolcsy; Barna Bordás, both of Budapest, Hungary

[73] Assignee: Eszakmagyarorszagi Vegyimuvek, Sajobabony, Hungary

[22] Filed: Dec. 18, 1974

[21] Appl. No.: 534,096

[30] Foreign Application Priority Data
Jan. 2, 1974   Hungary.............................. NO 178

[52] U.S. Cl. .................. 260/239 BF; 260/295 CA; 260/326.83; 260/455 A
[51] Int. Cl.² ............... C07D 223/02; C07C 155/02
[58] Field of Search..... 260/455 A, 239 BF, 293.74, 260/326.83, 295 CA

[56] References Cited
OTHER PUBLICATIONS
Amer. Chem. Journal Vol. 22 (1899) pp. 141–151.
J. Amer. Chem. Soc. 77; pp. 2479–2482 (1955).
J. Org. Chem. 44; pp. 1393–1399 (1971).
Helv. Chim. Acta. 2; pp. 118–132 (1919).

*Primary Examiner*—Lewis Gotts
*Assistant Examiner*—D. R. Phillip
*Attorney, Agent, or Firm*—Young & Thompson

[57] ABSTRACT

The invention relates to a new and advantageous process for the preparation of substituted S-alkyl thiocarbamates having the general formula (I),

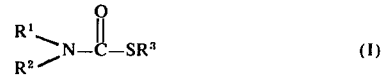 (I)

wherein
  $R^1$ stands for a $C_{1-4}$ alkyl group,
  $R^2$ stands for a $C_{1-4}$ alkyl or cyclohexyl group, or
  $R^1$ and $R^2$ may form together a $C_{4-6}$ polymethylene group, and
  $R^3$ stands for a $C_{2-3}$ alkyl group.

In accordance with the invention the substituted O-alkyl thiocarbamates of the general formula (II),

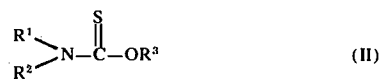 (II)

wherein $R^1$, $R^2$ and $R^3$ each have the same meanings as defined above, are subjected to isomerization by heating them at a temperature of 130° to 180°C in the presence of dimethyl sulfate or diethyl sulfate to yield the appropriate S-alkyl esters.

3 Claims, No Drawings

PROCESS FOR THE PREPARATION OF SUBSTITUTED S-ALKYL THIO-CARBAMATES

This invention relates to a novel process for the preparation of S-alkyl thiocarbamates having the general formula

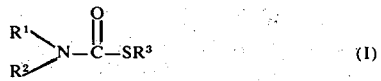

wherein
$R^1$ stands for a $C_{1-4}$ alkyl group,
$R^2$ stands for a $C_{1-4}$ alkyl or cyclohexyl group, or
$R^1$ and $R^2$ may form together a $C_{4-6}$ polymethylene group, and
$R^3$ stands for a $C_{2-3}$ alkyl group.

The compounds prepared according to the process of the invention are commonly known substances with favourable herbicidal properties. According to the literature these compounds can be prepared by three different basic procedures.

According to the British patent No. 808,753 and the U.S. Pat. No. 2,913,326 the compounds of the general formula (I) are prepared by reacting an appropriately substituted amine with phosgene in the presence of an acid binding agent, and treating the obtained carbamoyl chloride with a sodium alkanethiolate in an organic solvent under anhydrous conditions. The sodium alkanethiolate is prepared by reacting the appropriate alkanethiol with metallic sodium. According to an improved variant of this method, described by R. G. Campbell (U.S. Pat. No. 2,983,747), the carbamoyl chloride is reacted with the alkanethiol in the presence of anhydrous zinc chloride. This process eliminates the difficulties and risks of the use of metallic sodium.

According to the second basic procedure (see U.S. Pat. Nos. 3,175,817 and 3,185,720) a sodium alkanethiolate is reacted with phosgene in an organic solvent, and the resulting alkylthiocarbonyl chloride is reacted with the appropriate amine in the presence of an acid binding agent to obtain the desired S-alkyl thiocarbamate.

The third basic procedure consists in introducing carbon oxysulfide, under cooling, into the appropriate dialkylamine, and alkylating the obtained dialkylammonium dialkylthiocarbamate with a dialkyl sulfate to yield the desired S-alkyl thiocarbamate (see U.S. Pat. No. 3,133,947).

All the above basic procedures have, however, several disadvantages. Thus, the first and second methods involve the application of an organic solvent, such as toluene or xylene, under anhydrous conditions. These solvents are inflammable, hazardous to health, and relatively expensive. Thus, for economical reasons, the recovery of these solvents should be ensured. Both processes utilize phosgene, a highly toxic and inconvenient chemical, which, moreover, readily undergoes hydrolysis, and the resulting hydrochloric acid poses serious corrosion problems.

When utilizing phosgene in a chemical reaction severe precaution measures should be complied with, and corrosion-free, expensive equipment, which generally deteriorates within a short time, should be used. Further disadvantages arise from the inflammable, toxic and unpleasant nature of the alkanethiol reactants utilized.

Furthermore, the application of metallic sodium in plant-scale procedures, in great amounts, requires closed systems and special precaution measures.

Owing to the complicated preparation of carbon oxysulfide and to the relatively high cost of the alkylating agent, the third basic procedure has not become widespread in industrial practice.

Now we have found, unexpectedly, that the S-alkyl thiocarbamates can be prepared under very favourable conditions and with excellent yields by subjecting the appropriate O-alkyl thiocarbamates to isomerization in the presence of dimethyl sulfate or diethyl sulfate.

As known, substituted O-aryl thiocarbamates undergo such rearrangement when heated at 210°C for several hours (Bull. Chem. Soc. Japan 44, 1393 /1971/), but no rearrangement of the O-alkyl esters occurs upon heating.

Now we have found that when heating a substituted O-alkyl thiocarbamate at a temperature of about 160°C in the presence of a small amount, preferably 4 to 8 %, of dimethyl sulfate or diethyl sulfate and in the absence of solvent, the starting O-alkyl ester converts completely into the appropriate S-alkyl ester within 20 to 80 minutes.

The S-alkyl thiocarbamate is obtained generally with a yield of about 90% by distilling the reaction mixture in vacuum produced e.g. with a water-jet pump.

Accordingly, this invention relates to a process for the preparation of a substituted S-alkyl thiocarbamate having the general formula (I), in which a substituted O-alkyl thiocarbamate of the general formula (II),

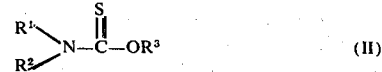

wherein $R^1$, $R^2$ and $R^3$ each have the same meanings as defined above, is subjected to isomerization by heating at a temperature of 130° to 180°C, preferably at 150° to 170°C, in the presence of dimethyl sulfate or diethyl sulfate.

The substituted O-alkyl thiocarbamates of the general formula (II), used as starting substances, are known compounds, and can be prepared by known procedures (see e.g. U.S. Pat. No. 3,224,863). Accordingly, sodium monochloroacetate is reacted with a potassium alkylxanthogenate in an aqueous solution, and the obtained carboxymethyl alkylxanthogenate is reacted in situ with a slight excess of the appropriate amine. The separated crude product is removed from the mixture, heated slightly in vacuo without drying, and then distilled. Thus the desired O-alkyl thiocarbamates can be obtained with an average yield of 70 %. These O-alkyl esters are non-corrosive liquids, and do not decompose at the temperature of isomerization.

The main advantages of the new process according to the invention are as follows:

No toxic reagents (phosgene, alkylthiols) need to be used, and it is unnecessary to maintain anhydrous conditions. The process can be performed very simply and easily, and no special and expensive precaution measures are required. The desired S-alkyl esters can usually be obtained with a yield of 90 %, but, since the unreacted O-alkyl esters separated by fractional distillation can be recirculated into the isomerization procedure, the actual conversion rate may well exceed 90 %. According to the references cited above, the known methods produce the S-alkyl thiocarbamates with yields of 55 to 98 %. Thus, in addition to the technological advantages discussed above, the yield of the new process according to the invention reaches or exceeds that obtainable with the best of the known processes.

The invention is elucidated by the aid of the following non-limiting Examples.

EXAMPLE 1

S-Ethyl N,N-dipropyl-thiocarbamate 94.5 g. (0.5 moles) of O-ethyl N,N-dipropyl-thiocarbamate are introduced into a 250 ml. round-bottomed flask, and 4.7 g. of diethyl sulfate are added. The mixture is refluxed for 80 minutes on an oil bath heated to 160°C. The progress of the reaction is monitored by sampling the reaction mixture and recording the UV spectra of the samples in methanol. The absorption maximum at 250 nm, characteristic of the =S group of the starting substance, gradually decreases, and disappears when the isomerization is completed. Then the reaction mixture is cooled, and the small amount of oily substance separated at the bottom of the flask is removed. The upper phase is distilled in vacuo. The title compound boils at 122°–124°C/19 Hgmm. 86.0 g. (91 %) of S-ethyl N,N-di-propyl-thiocarbamate are obtained; $n_D^{30} = 1.4750$.

Analysis: calculated: C, 57.01 %; H, 10.12 %; N, 7.40 %; S, 16.93 %. found: C, 57.08 %; H, 10.10 %; N, 7.32 %; S, 16.98 %.

EXAMPLE 2

S-Ethyl N,N-pentamethylene-thiocarbamate 86.5 g. (0.5 moles) of O-ethyl N,N-pentamethylene-thiocarbamate are introduced into a 250 ml. round-bottomed flask, and 4.3 g. of diethyl sulfate are added. The mixture is refluxed for 40 minutes on an oil bath heated to 160°C. The progress of the reaction is monitored as described in Example 1. When the isomerization is completed the reaction mixture is distilled, and the fraction boiling at 132°–134°C/20 Hgmm. is collected. 78 g. (90 %) of S-ethyl N,N-pentamethylene-thiocarbamate are obtained; $n_D^{24} = 1.5118$.

Analysis: calculated: C 55.45 %; H, 8.73 %; N, 8.09 %; S, 18.50 %. found: C, 55.38 %; H, 8.60 %; N, 8.11 %; S, 18.61 %.

EXAMPLE 3

S-Ethyl N,N-tetramethylene-thiocarbamate

The procedure described in Example 2 is repeated with the difference that an equivalent amount of O-ethyl N,N-tetramethylene-thiocarbamate is substituted for O-ethyl N,N-pentamethylene-thiocarbamate. The title compound is obtained with a yield of 91 %; b.p.: 136°–138°C/11 Hgmm., $n_D^{30} = 1.5150$.

EXAMPLE 4

S-Propyl N,N-dipropyl-thiocarbamate 61.0 g. (0.3 mole) of O-propyl N,N-dipropyl-thiocarbamate are introduced into a 100 ml. round-bottomed flask, and 3.0 g. of dimethyl sulfate are added. The mixture is refluxed for 80 minutes on an oil bath heated to 160°C, and then the product is isolated by vacuum distillation. 48.4 g. (81 %) of S-propyl N,N-dipropyl-thiocarbamate are obtained; b.p.: 132°–134°C/17 Hgmm., $n_D^{30} = 1.4736$.

Analysis: calculated: C, 59.07 %; H, 10.41 %; N, 6.89 %; S 15.77 %. found: C, 59.015 %; H, 10.40 %; N, 6.72 %; S, 15.86 %.

EXAMPLE 5

S-Ethyl N-ethyl-N-cyclohexyl-thiocarbamate

The procedure described in Example 4 is repeated but an equivalent amount of O-ethyl N-ethyl-N-cyclohexyl-thiocarbamate is substituted for O-propyl N,N-dipropyl-thiocarbamate. The title compound is obtaned with a yield of 80 %; b.p.: 142°–145°C/9 Hgmm., $n_D^{30} = 1.5049$.

EXAMPLE 6

S-Ethyl N,N-diisobutyl-thiocarbamate 43.4 g. (0.2 mole) of O-ethyl N,N-diisobutyl-thiocarbamate are introduced into a 100 ml. round-bottomed flask, and 2.5 g. of diethyl sulfate are added. The mixture is refluxed for 90 minutes on an oil bath heated to 160°C, and thereafter the product is isolated by vacuum distillation. 39.8 g. (92 %) of S-ethyl N,N-diisobutyl-thiocarbamate are obtained; b.p.: 137°–138°C/20 Hgmm., $n_D^{25} = 1.4689$.

Analysis: calculated: C, 60.78 %; H, 10.67 %; N, 6.52 %; S, 14.75 %. found: C, 60.63 %; H, 10.59 %; N, 6.49 %; S, 14.88 %.

EXAMPLE 7

S-Ethyl N,N-hexamethylene-thiocarbamate 56.2 g. (0.3 mole) of O-ethyl N,N-hexamethylene-thiocarbamate are introduced into a 100 ml. round-bottomed flask, and 3.5 g. of diethyl sulfate are added. The mixture is refluxed for 60 minutes on an oil bath heated to 160°C, and then the product is isolated by vacuum distillation. 49.4 g. (88 %) of S-ethyl N,N-hexamethylene-thiocarbamate are obtained; b.p.: 145°–146°C/17 Hgmm., $n_D^{25} = 1.5092$.

Analysis: calculated: C, 57.71 %; H, 9.15 %; N, 7.48 %; S, 17.12 %. found: C, 57.58 %; H, 9.22 %; N, 7.50 %; S, 17.05 %.

What is claimed is:

1. A process for the preparation of a substituted S-alkyl thiocarbamate having the formula,

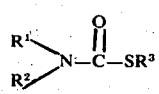

wherein $R^1$ stands for $C_{1-4}$ alkyl, $R^2$ stands for $C_{1-4}$ alkyl or cyclohexyl, or $R^1$ and $R^2$ may form together $C_{4-6}$ polymethylene, and $R^3$ stands for $C_{2-3}$ alkyl, in which a substituted O-alkyl thiocarbamate of the formula,

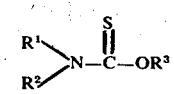

wherein $R^1$, $R^2$ and $R^3$ each have the same meanings as defined above, is subjected to isomerization by heating it at a temperature of 130° to 180°C, in the presence of dimethyl sulfate or diethyl sulfate.

2. A process as claimed in claim 1, in which the isomerization is carried out at a temperature of 150° to 170°C.

3. A process as claimed in claim 1, in which said dimethyl sulfate or diethyl sulfate is present in an amount of 4 to 8 % by weight of the starting substance.

* * * * *